United States Patent [19]

Nohda

[11] 4,370,034
[45] Jan. 25, 1983

[54] OPHTHALMOLOGICAL INSTRUMENT OF CONTINUOUSLY VARIABLE MAGNIFICATION

[75] Inventor: Masao Nohda, Yokohama, Japan

[73] Assignee: Nippon Kogaku K.K., Tokyo, Japan

[21] Appl. No.: 169,104

[22] Filed: Jul. 15, 1980

[30] Foreign Application Priority Data

Jul. 20, 1979 [JP] Japan .................................. 54-92331

[51] Int. Cl.³ .......................... A61B 3/14; G03B 29/00
[52] U.S. Cl. ...................................... 351/206; 354/62
[58] Field of Search ........................ 351/6, 7; 350/40; 354/62

[56] References Cited

U.S. PATENT DOCUMENTS 3,030,857  4/1962  Shumway ........................ 350/40 X
3,217,622  11/1965  Kiyono .................................. 351/7
4,265,518  5/1981  Matsumura ............................ 351/7

FOREIGN PATENT DOCUMENTS 2915639  10/1979  Fed. Rep. of Germany .

Primary Examiner—John K. Corbin
Assistant Examiner—Rodney B. Bovernick
Attorney, Agent, or Firm—Fitzpatrick, Cella, Harper & Scinto

[57] ABSTRACT

An ophthalmological instrument capable of continuously changing the size of an observed image is disclosed. The instrument comprises an image forming optical system for forming a first observed image, a magnification changing optical system for forming a second observed image from said first image and continuously changing the size of said second image and a correction member for correcting the optical length. To continuously change the size of said second image for observation, the magnification changing optical system includes a positive lens group and a negative lens group which are movable relative to each other in the direction of the optical axis. In order to keep constant the positions of the anterior and posterior focal points of the magnification changing optical system, that is, a composite system of the two lens groups, the optical length correction member is movable in association with the movements of the positive and negative lens groups.

6 Claims, 3 Drawing Figures

U.S. Patent  Jan. 25, 1983  4,370,034
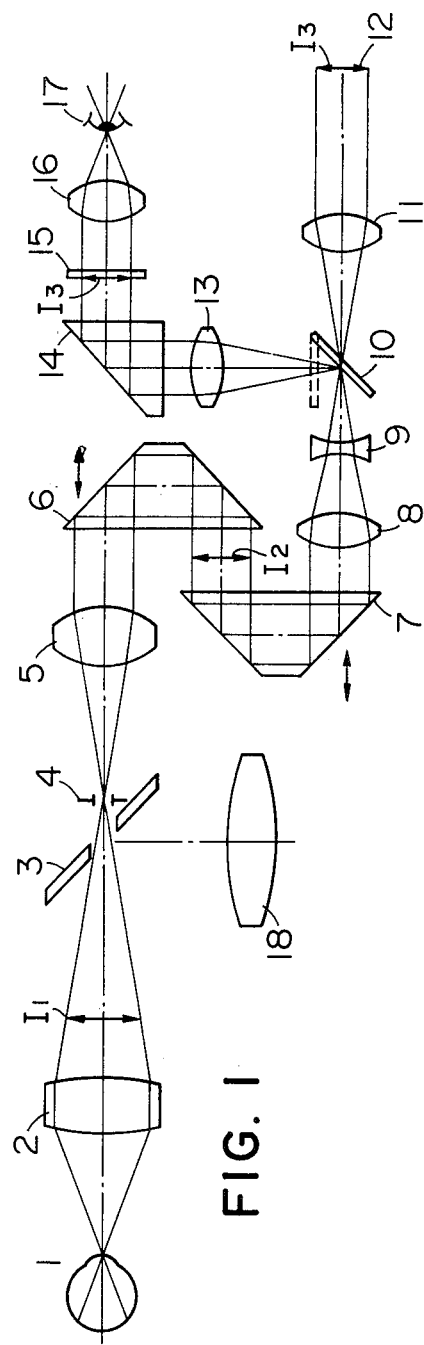
FIG. 1
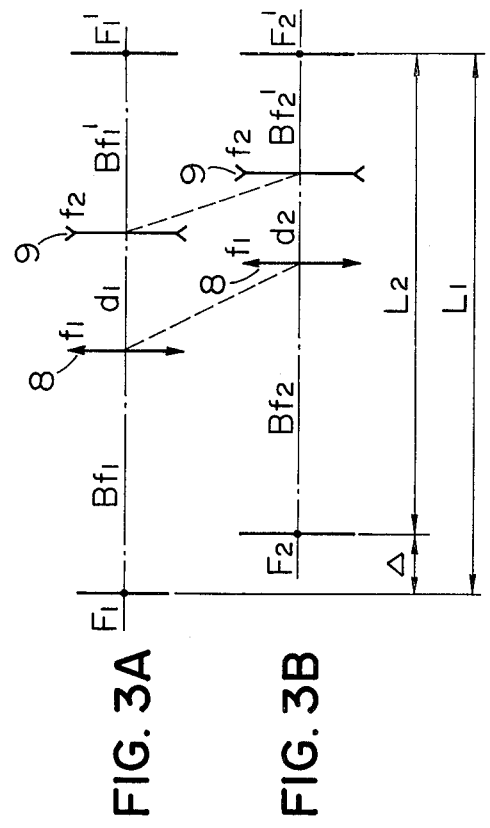
FIG. 3A
FIG. 3B
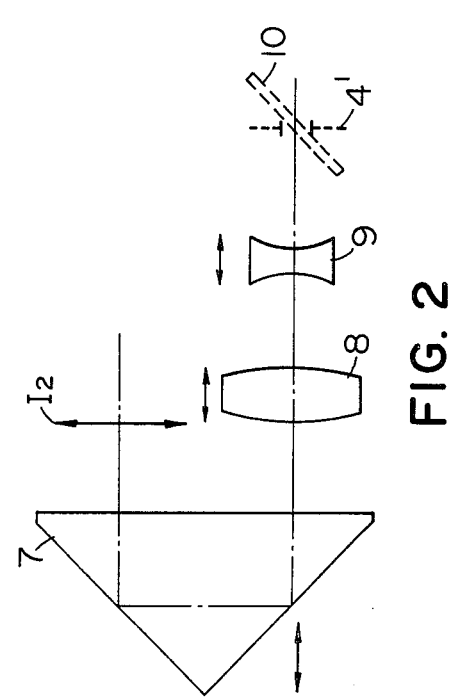
FIG. 2

OPHTHALMOLOGICAL INSTRUMENT OF CONTINUOUSLY VARIABLE MAGNIFICATION

BACKGROUND OF THE INVENTION

1. Field of the Invention

The present invention relates to an ophthalmological instrument such as a retinal camera. More particularly, the present invention relates to such ophthalmological instrument which is able to continuously change the magnification for observation or for picture taking.

2. Description of the Prior Art

In ophthalmological instruments such as retinal cameras there is used such optical system which produces no vignetting effect with respect to a diaphragm disposed conjugate with the cornea of an eye being examined. In such an optical system, the diaphragm conjugated with the cornea functions as a diaphragm for the whole optical system and also it determines the position of an eye point for observation. Ophthalmological instruments comprising such optical system have a disadvantage. As is known to those skilled in the art, the disadvantage is found in the fact that when the magnification for observation is continuously changed, the position of the eye point is also subjected to change which makes it difficult to obtain good observation.

SUMMARY OF THE INVENTION

Accordingly, it is a general object of the invention to eliminate the disadvantage mentioned above.

It is still a more specific object of the invention to provide an ophthalmological instrument in which the eye point can remain unchanged even when the magnification is continuously changed so that observation can be conducted easily and conveniently.

To attain the objects according to the invention there is provided an ophthalmological instrument of continuously variable magnification which comprises an image forming optical system including objective lens and relay lens for forming an image to be observed, a magnification changing optical system for continuously changing the size of said observed image and an optical length correcting member. When the magnification changing lens groups are moved, the optical length correcting member moves in coordination with the movements of the lens groups so as a keep fixed the positions of anterior and posterior focal points of the magnification changing optical system.

Other and further objects, features and advantages of the invention will appear more fully from the following description taken in connection with the accompanying drawings.

BRIEF DESCRIPTION OF THE DRAWINGS

FIG. 1 schematically shows an embodiment of the invention in which the present invention is embodied in a retinal camera;

FIG. 2 is a partly enlarged view of the embodiment showing in detail the arrangement of the right-angled prism for correcting optical length, and positive and negative lens groups constituting a magnification changing optical system; and FIGS. 3A and 3B show the basic arrangement of the magnification changing optical system in which FIG. 3A shows the optical system in a first magnification position and FIG. 3B shows it in a second magnification position.

DETAILED DESCRIPTION OF THE PREFERRED EMBODIMENTS

Referring first to FIG. 1 showing an embodiment of the invention, reference numeral 1 designates an eye to be examined. The beam of light from the subject eye 1 is at first collected through an objective lens 2 and then enters a relay lens 5 passing through the aperture of a bored reflecting mirror 3 and a diaphragm 4. Since the anterior focal point of the relay lens 5 lies in the vicinity of the diaphragm 4, the beam of light emerging from the relay lens 5 becomes a substantially parallel light beam. This parallel light beam enters a right-angled prism 6 disposed behind the relay lens 5. The beam is reflected twice by the right-angled prism 6 to reverse the beam toward a right-angled prism 7 for optical length correction which reflects the beam twice to direct it toward a magnification changing optical system comprising a positive lens group 8 and a negative lens group 9. The two lens groups 8 and 9 are movable relative to each other. Behind the magnification changing optical system there is provided a quick return mirror 10 which can be brought to a retracted position suggested by the dotted line away from the optical path. When the quick return mirror is retracted from the optical path, the beam of light emerging from the magnification changing optical system is allowed to enter a photographing lens 11 which focuses the beam upon a film surface 12. When the quick return mirror 10 is in the optical path, the mirror 10 reflects the beam to a relay lens 13. After being subjected to the action of the relay lens 13, the beam enters a prism 14 which reflects the beam toward a focal plate 15.

Designated by 18 is a projection lens which constitutes a part of a fundus illuminating optical system. In the fundus illuminating optical system, there are provided a ring slit conjugate with the cornea of the subject eye 1, a black point to be projected onto the objective lens 2 etc. not shown. The arrangement of such fundus illumination optical system is well known in the art and does not pertain directly to the present invention. Therefore, it need not be further described.

It is seen from FIG. 1 that a first fundus image $I_1$ of the subject eye 1 is formed between the objective lens 2 and bored mirror by the objective lens 2 and a second fundus image $I_2$ is formed between the focussing prism 6 and optical length correcting prism 7. The positions of the first and second fundus images $I_1$ and $I_2$ are variable depending upon the refractive power(diopter) of the subject eye 1. However, the position of the second fundus image $I_2$ can be maintained fixed by moving the focussing prism 6. In other words, the focussing right-angle prism 6 functions also as a visibility correcting member. A third fundus image $I_3$ is formed on the focal plate 15 when the mirror 10 is in the position indicated by the solid line or on the film surface 12 when the mirror 10 is in the retracted position indicated by the dotted line. The examiner's eye 17 positioned at the eye point can observe the third image $I_3$ on the focal plate 15 through an ocular 16. The diaphragm 4 is conjugate with the cornea of the subject eye 1 relative to the objective lens 2 and acts as a diaphragm for the entire system. The conjugate point thereof is the eye point for observation.

The arrangement of the optical length correcting prism 7, and positive and negative lens groups 8 and 9 in the above embodiment is further shown in FIG. 2. As previously noted, the positive and negative lens groups 8 and 9 constitute a magnification changing optical system according to the invention. Also, as described above, the second fundus image I₂ is formed at a fixed position by moving the focussing prism 6 irrespective of the diopter of the subject eye 1. Through the relay lens 5 and the magnification changing optical system 8, 9, an image 4' of the diaphragm 4 is formed behind the optical system 8, 9. In practice, the beam has the smallest width at this position of the diaphragm image 4' and therefore the quick return mirror 10 is located in this place.

Magnification is changed by moving the positive and negative lens groups 8 and 9 relative to each other. If the position of the diaphragm image 4' can be maintained unchanged at the time of the magnification being changed by relative movement of the lens groups 8 and 9, then the point conjugate with the diaphragm image 4' by the after-connected optical system, that is, the eye point will remain unchanged and take always a fixed position. To satisfy the condition, the anterior and posterior focal points of the magnification changing optical system that is a composite system of the positive and negative lens groups 8 and 9 should be kept in fixed positions without being changed with the change of magnification. According to the shown embodiment this is attained by the optical length correcting prism 7 which is movable in the direction of the optical axis to perform the function.

Referring to FIGS. 3A and 3B showing the basic arrangement of the magnification changing optical system, $f_1$ and $f_2$ are focal lengths of the positive and negative lens groups 8 and 9 respectively. In a first position shown in FIG. 3A, the two lens groups 8 and 9 are so disposed as to have a distance $d_1$ therebetween. The magnification changing optical system, that is, the composite system of the two lens groups 8 and 9 has its anterior focal point at $F_1$ which is $Bf_1$ distant from the positive lens group 8. $Bf'_1$ is the distance from the negative lens group 9 to the posterior focal point $F'_1$ of the magnification changing optical system. To change the magnification, the lens groups are moved to a second position as shown in FIG. 3B in which the distance between the lens groups 8 and 9 is $d_2$. Let $Bf_2$ be the distance between the anterior focal point $F_2$ and the positive lens group 8, and $Bf'_2$ be that between the posterior focal point $F'_2$ and the negative lens group 9. Then, there hold:

$$Bf_1 = \frac{f_1(f_2 - d_1)}{f_1 + f_2 - d_1},$$

$$Bf'_1 = \frac{f_2(f_1 - d_1)}{f_1 + f_2 - d_1},$$

$$Bf_2 = \frac{f_1(f_2 - d_2)}{f_1 + f_2 - d_2},$$

$$Bf'_2 = \frac{f_2(f_1 - d_2)}{f_1 + f_2 - d_2}.$$

Assuming that the distance between the anterior and posterior focal points of the magnification changing optical system in the first position is $L_1$ and that in the second position is $L_2$, then $$L_1 = Bf_1 + d_1 + Bf'_1$$

$$L_2 = Bf_2 + d_2 + Bf'_2.$$

Therefore, the amount of change $\Delta$ is:

$$\Delta = L_1 - L_2$$

The function of the optical length correcting prism 7 is to correct the change $\Delta$. Namely, the prism 7 is moved by a distance $a$ as given by:

$$a = \frac{\Delta}{2} = \frac{L_1 - L_2}{2}$$

By moving the prism 7 in this manner, the anterior and posterior focal points of the magnification changing optical system can remain always unchanged and therefore the eye point can be kept in a fixed position without being changed with the change of magnification.

In the shown embodiment, as seen from FIGS. 3A and 3B, the magnification is changed by moving the lens groups 8 and 9 while keeping the posterior focal point in a fixed position. At the same time, the anterior focal point is kept constant by the optical length correcting prism. This enables manufacture of a compact apparatus having the shortest possible optical length as a whole. However, various modifications can be made to the shown embodiment within the scope of the invention. For example, the arrangement of the apparatus can be modified in such manner that the magnification may be changed while keeping the anterior focal point in a fixed position and correcting the position of the posterior focal point by the optical length correcting prism for maintaining the latter unchanged.

As is understood from the foregoing, according to the invention there is provided an ophthalmological instrument in which the eye point can remain unchanged even when the magnification is continuously changed during the observation of image and which is easy to operate and assures good observation.

I claim:

1. An ophthalmological apparatus capable of changing the magnification of an image to be observed and maintaining an eye point unchanged when the magnification is changed, comprising:
    (a) an image forming means for forming a first image to be observed;
    (b) a diopter correcting means for keeping the position of said first image constant irrespective of the diopter of the eye to be examined;
    (c) a magnification changing optical system for forming a second image from said first image and changing the size of said second image, said magnification changing means having movable lens groups which are movable relative to each other in the direction of optical axis; and
    (d) an optical path length correcting means for correcting an optical path length between the anterior and the posterior focal points of said magnification changing optical system, said optical path length correcting means including reflecting member movable along the optical axis of said magnification changing optical system in association with the movement of said movable lens groups to reflect the light beam from said first image to said magnification changing optical system.

2. An ophthalmological apparatus according to claim 1, wherein said reflecting member of said optical path length correcting means is a right-angled prism having reflecting surfaces intersecting at right angles.

3. An ophthalmological apparatus according to claim 2, wherein said diopter correcting means including a right-angled prism having reflecting surfaces intersecting at right angles movable along the optical axis of said image forming means.

4. An ophthalmological instrument according to claim 3, wherein when said magnification changing optical system is moved from a first position to a second one, the distance between the anterior and posterior focal points of said optical system is changed from $L_1$ to $L_2$ wherein $$L_1 = Bf_1 - d_1 + Bf'_1$$

$$L_2 = Bf_2 + d_2 + Bf'_2$$

wherein, $f_1$ is focal length of the positive lens group of said magnification changing optical system, $f_2$ is focal length of the negative lens group thereof, $d_1$ is the distance between said two legs groups in the first position, $d_2$ is the distance between said two lens groups in the second position, $Bf_1$ is the distance from the anterior focal point to the positive lens group in the first position, namely $$Bf_1 = \frac{f_1(f_2 - d_1)}{f_1 + f_2 - d_1},$$

$Bf'_1$ is the distance from the posterior focal point to the negative lens group in the first position, namely $$Bf'_1 = \frac{f_2(f_1 - d_1)}{f_1 + f_2 - d_1}$$

$Bf_2$ is the distance from the anterior focal point to the positive lens group in the second position, namely $$Bf_2 = \frac{f_1(f_2 - d_2)}{f_1 + f_2 - d_2} \text{ and}$$

$Bf'_2$ is the distance from the posterior focal point to the negative lens group in the second position, namely $$Bf'_2 = \frac{f_2(f_1 - d_2)}{f_1 + f_2 - d_2},$$

and at the same time said right-angled optical length correcting prism is moved by a distance $a$ given by the following equation:

$$a = (L_1 - L_2)/2$$

wherein, $L_1$ and $L_2$ have the same meaning as above.

5. An ophthalmological instrument according to claim 4, wherein said diopter correcting means are disposed between said image forming means and optical path length correcting means, said diopter correcting means being movable in the direction of optical axis to keep the position of said first image constant irrespective of the diopter of the eye to be examined.

6. An ophthalmological instrument according to claim 5, wherein said image forming means includes an objective lens and a relay lens for retinal camera.

* * * * *

UNITED STATES PATENT AND TRADEMARK OFFICE
CERTIFICATE OF CORRECTION

PATENT NO. : 4,370,034

DATED : January 25, 1983

INVENTOR(S) : MASAO NOHDA

It is certified that error appears in the above-identified patent and that said Letters Patent is hereby corrected as shown below:

Claim 4, line 12, "legs" should be --lens--.

Signed and Sealed this

Fifth Day of April 1983

[SEAL]

Attest:

GERALD J. MOSSINGHOFF

Attesting Officer     Commissioner of Patents and Trademarks